(12) United States Patent
Chang et al.

(10) Patent No.: US 7,453,020 B2
(45) Date of Patent: Nov. 18, 2008

(54) MOLECULAR SIEVE CATALYST COMPOSITION, ITS MAKING AND USE IN CONVERSION PROCESSES

(75) Inventors: Yun Feng Chang, Houston, TX (US);
Luc R. M. Martens, Meise (BE);
Stephen Neil Vaughn, Kingwood, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 725 days.

(21) Appl. No.: 11/109,586

(22) Filed: Apr. 19, 2005

(65) Prior Publication Data

US 2006/0173230 A1    Aug. 3, 2006

Related U.S. Application Data

(60) Provisional application No. 60/650,052, filed on Feb. 4, 2005, provisional application No. 60/648,878, filed on Jan. 31, 2005, provisional application No. 60/648,946, filed on Jan. 31, 2005.

(51) Int. Cl.
*C07C 1/00* (2006.01)

(52) U.S. Cl. ..................... 585/640; 585/639

(58) Field of Classification Search .......... 585/638–640
See application file for complete search history.

(56) References Cited

U.S. PATENT DOCUMENTS

| 4,062,905 A | 12/1977 | Chang et al. ............... 260/682 |
| 4,079,095 A | 3/1978 | Givens et al. ............... 260/682 |
| 4,247,731 A * | 1/1981 | Wunder et al. ............... 585/640 |
| 4,310,440 A | 1/1982 | Wilson et al. ............... 252/435 |
| 4,440,871 A | 4/1984 | Lok et al. ............... 502/214 |
| 5,367,100 A | 11/1994 | Gongwei et al. ............ 585/640 |
| 6,503,863 B2 | 1/2003 | Fung et al. ............... 502/214 |
| 6,541,415 B2 | 4/2003 | Vaughn et al. ............. 502/214 |
| 6,660,682 B2 | 12/2003 | Cao et al. ............... 502/214 |
| 6,787,501 B2 | 9/2004 | Chang et al. ............... 502/214 |
| 2003/0181322 A1 | 9/2003 | Chang et al. ............... 502/214 |

FOREIGN PATENT DOCUMENTS

| WO | WO 02/070407 | 9/2002 |
| WO | 03/000412 | 1/2003 |
| WO | 03/000413 | 1/2003 |
| WO | WO 2004/060559 | 7/2004 |
| WO | WO 2005/035120 | 4/2005 |

* cited by examiner

*Primary Examiner*—Glenn Caldarola
*Assistant Examiner*—In Suk Bullock

(57) ABSTRACT

A catalyst composition that comprises an over flocculated molecular sieve and optionally, a phosphorous compound and, optionally, a non-over flocculated molecular sieve. A method of preparing a catalyst composition that comprises mixing an over flocculated molecular sieve and optionally, a phosphorous compound and, optionally, a non-over flocculated molecular sieve.

30 Claims, No Drawings

MOLECULAR SIEVE CATALYST COMPOSITION, ITS MAKING AND USE IN CONVERSION PROCESSES

CROSS REFERENCE TO RELATED APPLICATIONS

This application claims the benefit of U.S. Provisional Application No. 60/650,052 filed Feb. 4, 2005, U.S. Provisional Application No. 60/648,878, filed Jan. 31, 2005, and U.S. Provisional Application No. 60/648,946, filed Jan. 31, 2005, the disclosures of which are fully incorporated herein by reference.

FIELD OF THE INVENTION

The present invention relates to a molecular sieve catalyst composition, to a method of making or forming the molecular sieve catalyst composition, and to a conversion process using the molecular sieve catalyst composition.

BACKGROUND OF THE INVENTION

Olefins are traditionally produced from petroleum feedstock by catalytic or steam cracking processes. These cracking processes, especially steam cracking, produce light olefin(s) such as ethylene and/or propylene from a variety of hydrocarbon feedstock. Ethylene and propylene are important commodity petrochemicals useful in a variety of processes for making plastics and other chemical compounds.

The petrochemical industry has known that oxygenates, especially alcohols, are convertible into light olefin(s). There are numerous technologies available for producing oxygenates including fermentation or reaction of synthesis gas derived from natural gas, petroleum liquids, carbonaceous materials including coal, recycled plastics, municipal waste or any other organic material. Generally, the production of synthesis gas involves a combustion reaction of natural gas, mostly methane, and an oxygen source into hydrogen, carbon monoxide and/or carbon dioxide. Syngas production processes are well known, and include conventional steam reforming, autothermal reforming or a combination thereof.

Methanol, the preferred alcohol for light olefin production, is typically synthesized from the catalytic reaction of hydrogen, carbon monoxide and/or carbon dioxide in a reactor in the presence of a heterogeneous catalyst. For example, in one synthesis process methanol is produced using a copper/zinc oxide catalyst in a water-cooled tubular reactor. The preferred methanol conversion process is generally referred to as a methanol-to-olefin(s) process (MTO), where an oxygenate, typically mostly methanol, is converted into primarily ethylene and/or propylene in the presence of a molecular sieve.

There are many different types of molecular sieves well known to convert a feedstock, especially an oxygenate containing feedstock, into one or more olefin(s). Molecular sieves, such as zeolites or zeolite-type molecular sieves, carbons and oxides, are porous solids having pores of different sizes that selectively adsorb molecules that can enter the pores, and exclude other molecules that are too large. Examples of molecular sieves useful in converting an oxygenate into olefin(s) are: U.S. Pat. No. 5,367,100 describes the use of a well known zeolite, ZSM-5, to convert methanol into olefin(s); U.S. Pat. No. 4,062,905 discusses the conversion of methanol and other oxygenates to ethylene and propylene using crystalline aluminosilicate zeolites, for example Zeolite T, ZK5, erionite and chabazite; U.S. Pat. No. 4,079,095 describes the use of ZSM-34 to convert methanol to hydrocarbon products such as ethylene and propylene; U.S. Pat. No. 4,310,440 describes producing light olefin(s) from an alcohol using a crystalline aluminophosphates, often represented by $ALPO_4$; and U.S. Pat. No. 4,440,871 describes silicoaluminophosphate molecular sieves (SAPO), one of the most useful molecular sieves for converting methanol into olefin(s).

Typically, molecular sieves are formed into molecular sieve catalyst compositions to improve their durability in commercial conversion processes. The collisions within a commercial process between catalyst composition particles themselves, the reactor walls, and other reactor systems cause the particles to breakdown into smaller particles called fines. The physical breakdown of the molecular sieve catalyst composition particles is known as attrition. Problems develop in the recovery systems because fines often exit the reactor in the product containing effluent stream. Catalyst compositions having a higher resistance to attrition generate fewer fines; this results in improved process operability, and less catalyst composition being required for a conversion process, and therefore, lower overall operating costs.

It is known that the way in which the molecular sieve catalyst compositions are made or formulated affects catalyst composition attrition. Molecular sieve catalyst compositions are formed by combining a molecular sieve and a matrix material usually in the presence of a binder. For example, PCT Patent Publication WO 03/000413 A1 published Jan. 3, 2003 discloses a low attrition molecular sieve catalyst composition using a synthesized molecular sieve that has not been fully dried, or partially dried, in combination in a slurry with a binder and/or a matrix material. Also, PCT Patent Publication WO 03/000412 A1 published Jan. 3, 2003 discusses a low attrition molecular sieve catalyst composition produced by controlling the pH of the slurry away from the isoelectric point of the molecular sieve. U.S. Pat. No. 6,787,501 shows making a low attrition molecular sieve catalyst composition by making a slurry of a synthesized molecular sieve, a binder, and optionally a matrix material, wherein 90 percent by volume of the slurry contains particles having a diameter less than 20 µm. U.S. Patent Application Publication No. U.S. 2003/0181322 published Sep. 25, 2003, which is herein fully incorporated by reference, illustrates making an attrition resistant molecular sieve catalyst composition by controlling the ratio of a binder to a molecular sieve. U.S. Pat. No. 6,503,863 is directed to a method of heat treating a molecular sieve catalyst composition to remove a portion of the template used in the synthesis of the molecular sieve. U.S. Pat. No. 6,541,415 describes improving the attrition resistance of a molecular sieve catalyst composition that contains molecular sieve-containing recycled attrition particles and virgin molecular sieve. U.S. Pat. No. 6,660,682 describes the use of a polymeric base to reduce the amount of templating agent required to produce a particular molecular sieve.

It is also known that in typical commercial processes that flocculants are used in the recovery of synthesized molecular sieves. These flocculants are known to facilitate the crystal recovery and to increase the yield of recovery of the synthesized molecular sieve typically in a large scale commercial process. However, the presence of a flocculate can affect the catalyst formulation, and in some cases flocculation can result in the formulation of catalyst compositions having lower attrition resistance, lower selectivity in various conversion processes, and high slurry viscosity.

Although these molecular sieve catalyst compositions described above are useful in hydrocarbon conversion processes, it would be desirable to have an improved molecular sieve catalyst composition having better attrition performance and lower slurry viscosity.

SUMMARY OF THE INVENTION

This invention generally provides for a method of formulating a molecular sieve catalyst composition and to its use in a conversion process for converting a feedstock into one or more olefin(s).

In one embodiment the invention is directed to a catalyst composition prepared by the process comprising combining an over flocculated molecular sieve, a binder, optionally a matrix material, optionally a non-over flocculated molecular sieve, and optionally a phosphorous compound, preferably an acidic phosphorous compound to form a catalyst slurry; and milling the catalyst slurry. The above embodiment can be combined with any one or more of the various embodiments described below.

In another embodiment, the invention relates to a catalyst composition prepared by the process comprising combining an over flocculated molecular sieve recovered with a first flocculant, a binder, optionally a matrix material, optionally a non-over flocculated molecular sieve recovered with a second flocculant, and optionally a phosphorous compound, preferably an acidic phosphorous compound to form a catalyst slurry; and milling the catalyst slurry. In one embodiment, the first flocculant has an average molecular weight of about 500 to about 50,000,000. In another embodiment, the second flocculant has an average molecular weight of about 300,000 to about 30,000,000. In one embodiment, the phosphorous compound is selected from, but not limited to, phosphoric acid, phosphorous acid, polyphosphoric acid, ammonium dihydrogen phosphate, ammonium hydrogen phosphate, pyrophosphoric acid, orthophosphoric acid, hypophosphorous acid.

In another embodiment, the invention relates to a method of preparing a catalyst composition comprising combining an over flocculated molecular sieve, a binder, optionally a matrix material, optionally a non-over flocculated molecular sieve, and optionally with a phosphorous compound, preferably an acidic phosphorous compound to form a catalyst slurry; and milling the catalyst slurry.

In another embodiment, the invention relates to a process for producing one or more olefin(s), the process comprising the steps of (a) introducing a feedstock to a reactor system in the presence of a molecular sieve catalyst composition prepared by the method comprising the steps of: (i) combining: (A) an over flocculated molecular sieve recovered with a first flocculant, (B) a binder, (C) optionally, a matrix material, (D) optionally a non-over flocculated molecular sieve recovered with a second flocculant, and (E) optionally a phosphorous compound to form a catalyst slurry; and (ii) milling the catalyst slurry; (b) withdrawing from the reactor system an effluent stream; and (c) passing the effluent gas through a recovery system recovering at least the one or more olefin(s).

In another preferred embodiment, the invention relates to an integrated process for making one or more olefin(s), the integrated process comprising the steps of (a) passing a hydrocarbon feedstock to a syngas production zone to produce a synthesis gas stream; (b) contacting the synthesis gas stream with a catalyst to form an oxygenated feedstock; and (c) converting the oxygenated feedstock into the one or more olefin(s) in the presence of a molecular sieve catalyst composition, the molecular sieve catalyst composition prepared by the method comprising the steps of: (i) combining: (A) an over flocculated molecular sieve recovered with a first flocculant, (B) a binder, (C) optionally, a matrix material, (D) optionally a non-over flocculated molecular sieve recovered with a second flocculant, and (E) optionally a phosphorous compound to form a catalyst slurry; and (ii) milling the catalyst slurry.

DETAILED DESCRIPTION OF THE INVENTION

Introduction

The invention is directed toward a molecular sieve catalyst composition, its making, and its use in the conversion of a feedstock into one or more olefin(s). A formulated molecular sieve catalyst composition is typically formed from a slurry of the combination of a molecular sieve, a binder, and optionally, most preferably, a matrix material. It has been discovered that the presence of an excess of flocculent, which may result in an over flocculated molecular sieve, can result in processing difficulties, such as a high viscosity. This invention is directed toward a catalyst composition and method of making and using the catalyst composition, that comprises the over flocculated molecular sieve. It has been discovered that an over flocculated molecular sieve that forms a slurry, which is milled, preferably bead milled, that can exhibit improved properties, e.g., lower slurry viscosity and better attrition performance when it is formed into shaped particles, e.g., spray drying. Furthermore, a synergistic effect has been discovered wherein an over flocculated molecular sieve and optionally a phosphorous compound, for example phosphoric acid, and/or optionally, a non-over flocculated molecular sieve are combined to form a slurry, which is milled, preferably bead milled, that can exhibit improved properties, e.g., lower slurry viscosity and better attrition performance when it is formed into shaped particles, e.g., spray drying.

Molecular Sieves

Molecular sieves have various chemical, physical, and framework characteristics. Molecular sieves have been well classified by the Structure Commission of the International Zeolite Association (IZA) according to the rules of the IUPAC Commission on Zeolite Nomenclature. A framework-type describes the connectivity, topology, of the tetrahedrally coordinated atoms constituting the framework, and making an abstraction of the specific properties for those materials. Framework-type zeolite and zeolite-type molecular sieves for which a structure has been established, are assigned a three letter code and are described in the *Atlas of Zeolite Framework Types*, 5th edition, Elsevier, London, England (2001), which is herein fully incorporated by reference. For additional information on molecular sieve types, structures and characteristics, see van Bekkum, et al., *Introduction to Zeolite Science and Practice, Second Completely Revised and Expanded Edition*, Volume 137, Elsevier Science, B.V., Amsterdam, Netherlands (2001), which is also fully incorporated herein by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEI, AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI topology or a CHA topology, or a combination thereof, most preferably an intergrowth thereof.

The small, medium and large pore molecular sieves have from a 4-ring to a 12-ring or greater framework-type. In a preferred embodiment, the molecular sieves have 8-, 10- or 12-ring structures or larger and an average pore size in the range of about 3 Å to 15 Å. In the most preferred embodiment, the molecular sieves, preferably SAPO molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves based on silicon, aluminum, and phosphorous, and metal containing molecular sieves thereof, have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683, 217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO$_4$), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758, 419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500,651, 4,551,236 and 4,605, 492 (TiAPO), U.S. Pat. Nos. 4,824,554, 4,744,970 (CoAPSO), U.S. Pat. No. 4,735,806 (GaAPSO), EP-A-0 293 937 (QAPSO, where Q is framework oxide unit [QO$_2$]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,098,684 (MCM-41), U.S. Pat. No. 5,198,203 (MCM-48), U.S. Pat. Nos. 5,241,093, 5,304,363 (MCM-50), U.S. Pat. Nos. 5,493,066, 5,675,050, 6,077,498 (ITQ-1), U.S. Pat. No. 6,409,986 (ITQ-5), U.S. Pat. No. 6,419,895 (UZM-4), U.S. Pat. No. 6,471,939 (ITQ-12), U.S. Pat. No. 6,471,941 (ITQ-13), U.S. Pat. No. 6,475, 463 (SSZ-55), U.S. Pat. No. 6,500,404 (ITQ-3), U.S. Pat. No. 6,500,998 (UZM-5 and UZM-6), U.S. Pat. No. 6,524,551 (MCM-58) and U.S. Pat. No. 6,544,495 (SSZ-57), U.S. Pat. No. 6,547,958 (SSZ-59), U.S. Pat. No. 6,555,090 (ITQ-36) and U.S. Pat. No. 6,569,401 (SSZ-64), all of which are herein fully incorporated by reference. Other molecular sieves are described in R. Szostak, *Handbook of Molecular Sieves*, Van Nostrand Reinhold, New York, N.Y. (1992), which is herein fully incorporated by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves.

In one embodiment, the molecular sieve, as described in many of the U.S. patents mentioned above, is represented by the empirical formula, on an anhydrous basis:

$$mR:(M_xAl_yP_z)O_2$$

wherein R represents at least one templating agent, preferably an organic templating agent; m is the number of moles of R per mole of $(M_xAl_yP_z)O_2$ and m has a value from 0 to 1, preferably from 0 to 0.5, and most preferably from 0 to 0.3; x, y, and z represent the mole fraction of metal M (other than Al or P), Al, P respectively, and M as tetrahedral oxides, where M is a metal selected from one of Group IA, IIA, IB, IIIB, IVB, VB, VIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Synthesis of a molecular sieve, especially a SAPO molecular sieve, its formulation into a SAPO catalyst, and its use in converting a hydrocarbon feedstock into olefin(s), is shown in, for example, U.S. Pat. Nos. 4,499,327, 4,677,242, 4,677, 243, 4,873,390, 5,095,163, 5,714,662 and 6,166,282, all of which are herein fully incorporated by reference. Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof. The more preferred molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof.

In an embodiment, the molecular sieve is an intergrowth material having two or more distinct phases of crystalline structures within one molecular sieve composition. In particular, SAPO intergrowth molecular sieves are described in the U.S. Pat. No. 6,812,372, PCT Publication WO 02/070407 published Sep. 12, 2002 and PCT Publication WO 98/15496 published Apr. 16, 1998, which are herein fully incorporated by reference. For example, SAPO-18, ALPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the molar ratio of CHA to AEI is greater than 1:1.

Molecular Sieve Synthesis

Generally, molecular sieves are synthesized by the hydrothermal crystallization of one or more of a source of aluminum, a source of phosphorous, a source of silicon, a templating agent, and a metal containing compound. Typically, a combination of sources of silicon, aluminum and phosphorous, optionally with one or more templating agents and/or one or more metal containing compounds, are placed in a sealed pressure vessel, optionally lined with an inert plastic such as polytetrafluoroethylene, and heated, under a crystallization pressure and temperature, at static or stirred conditions, until a crystalline material is formed in a synthesis mixture. Then, in a commercial process in particular, one or more flocculant(s) is added to the synthesis mixture to speed up settling of the crystals and to achieve phase separation, i.e., a solids-rich phase in the lower portion of the vessel and a solids-free or solids-lean liquid layer in the upper portion of the vessel. A portion of the upper liquid layer is removed, decanted, or reduced in quantity. The remaining flocculated product containing the crystalline molecular sieve is then, optionally, contacted with the same or a different fresh liquid, typically with water, in a washing step, from once to many times depending on the desired purity of the supernatant, liquid portion, of the synthesis mixture being removed. It is also optional to repeat this process by adding in additional flocculant followed by additional washing steps. Then, the crystallized molecular sieve is recovered by filtration, centrifugation and/or decanting. Preferably, the molecular sieve is filtered using a filter that provides for separating certain crystal sized molecular sieve particles from any remaining liquid portion that may contain different size molecular sieve crystals.

In a preferred embodiment the molecular sieves are synthesized by forming a reaction product or synthesis mixture of a source of silicon, a source of aluminum, a source of phosphorous and an organic templating agent, preferably a nitrogen containing organic templating agent. This particularly preferred embodiment results in the synthesis of a silicoaluminophosphate crystalline material in a synthesis mixture. One or more flocculants are added to the synthesis mixture, and the crystallized molecular sieve is then removed or isolated by filtration, centrifugation and/or decanting.

Non-limiting examples of silicon sources include a silicates, fumed silica, for example, Aerosil-200 available from Degussa Inc., New York, N.Y., and CAB-O-SIL M-5, silicon compounds such as tetraalkyl orthosilicates, for example, tetramethyl orthosilicate (TMOS) and tetraethylortho silicate (TEOS), colloidal silicas or aqueous suspensions thereof, for example Ludox-HS-40 sol available from E.I. du Pont de Nemours, Wilmington, Del., silicic acid, alkali-metal silicate, or any combination thereof. The preferred source of silicon is a silica sol, such as Nalco colloidal silica, available from Nalco Chemical, Sugarland, Tex.

Non-limiting examples of aluminum sources include aluminum-containing compositions such as aluminum alkoxides, for example aluminum isopropoxide, aluminum phosphate, aluminum hydroxide, sodium aluminate, pseudo-boehmite, gibbsite and aluminum trichloride, or any combinations thereof. A preferred source of aluminum is pseudo-boehmite, particularly when producing a silicoaluminophosphate molecular sieve.

Non-limiting examples of phosphorous sources, which may also include aluminum-containing phosphorous compositions, include phosphorous-containing, inorganic or organic, compositions such as phosphoric acid, organic phosphates such as triethyl phosphate, and crystalline or amorphous aluminophosphates such as $AlPO_4$, phosphorous salts, or combinations thereof. The preferred source of phosphorous is phosphoric acid, particularly when producing a silicoaluminophosphate.

Templating agents are generally compounds that contain elements of Group VA of the Periodic Table of Elements, particularly nitrogen, phosphorus, arsenic and antimony, more preferably nitrogen or phosphorous, and most preferably nitrogen. Typical templating agents of Group VA of the Periodic Table of elements also contain at least one alkyl or aryl group, preferably an alkyl or aryl group having from 1 to 10 carbon atoms, and more preferably from 1 to 8 carbon atoms. The preferred templating agents are nitrogen-containing compounds such as amines and quaternary ammonium compounds.

The quaternary ammonium compounds, in one embodiment, are represented by the general formula $R_4N^+$, where each R is hydrogen or a hydrocarbyl or substituted hydrocarbyl group, preferably an alkyl group or an aryl group having from 1 to 10 carbon atoms. In one embodiment, the templating agents include a combination of one or more quaternary ammonium compound(s) and one or more of a mono-, di- or tri-amine.

Non-limiting examples of templating agents include tetraalkyl ammonium compounds including salts thereof such as tetramethyl ammonium compounds including salts thereof. The preferred templating agent or template is a tetraethylammonium compound, tetraethyl ammonium hydroxide (TEAOH) and salts thereof, particularly when producing a SAPO molecular sieve.

Flocculants

When commercially recovering any of the molecular sieves discussed above, typically one or more chemical reagents are added to the crystallization vessel or synthesis reactor after crystallization is substantially complete, preferably complete. Optionally, the synthesis mixture is transferred to another vessel separate from the reaction vessel or the vessel in which crystallization occurs, and a flocculant is then added to this other vessel from which the crystalline molecular sieve is ultimately recovered. These chemical reagents or flocculants are used to increase the recovery rate of the molecular sieve crystals and increase the yield of the synthesized molecular sieve crystals. While not wishing to be bound to any particular theory, these flocculants act either as (1) a surface charge modifier that results in the agglomeration of very small particles into larger aggregates of molecular sieve particles; (2) surface anchors that bridge many small particles to form aggregates of molecular sieve particles; or (3) spacers to prevent crystals from packing too closely that may restrict liquid flow during filtration and washing. The aggregates of the molecular sieve crystals are then easily recovered by well known techniques such as filtration or through a filter press process.

The flocculant is added to the synthesis mixture after crystallization has occurred from the combination of one or more of a silicon source, a phosphorous source, an aluminum source, and a templating agent. The synthesized molecular sieve is then recovered by filtration, however, optionally, the synthesized molecular sieve is washed and additional flocculant is used to further aggregate any remaining synthesized molecular sieve from the liquid portion of the synthesis mixture.

There are many types of flocculants, including both inorganic and organic flocculants. Inorganic flocculants are typically aluminum or iron salts that form insoluble hydroxide precipitates in water. Non-limiting examples such as aluminum sulfate, poly(aluminum chloride), sodium aluminate, iron (III)-chloride and sulfate, iron (II) sulfate, and sodium silicate (activated silica). The major classes of organic flocculants are: (1) nonionic flocculant, for example, polyethylene oxide, polyacrylamide (PAM), partially hydrolyzed polyacrylamide (HPAM), and dextran; (2) cationic flocculant, for example, polyethyleneimine (PEI), polyacrylamide-co-trimethylammonium, ethyl methyl acrylate chloride (PTAMC), and poly (N-methyl-4-vinylpyridinium iodide); and (3)

anionic flocculant, for example, poly (sodium acrylate), dextran sulfates, and/or high molecular weight ligninsulfonates prepared by a condensation reaction of formaldehyde with ligninsulfonates, and polyacrylamide. Where the synthesis mixture includes the presence of water, it is preferable that the flocculant used is water soluble. Additional information on flocculation is discussed in G. J. Fleer and J. H. M. Scheutjens, *Coagulation and Flocculation Theory and Applications*, ed. by B. Döbias, pp. 209-263, Marcel Dekker, New York, 1993, which is fully incorporated by reference.

The flocculant may be added to the synthesis mixture after crystallization in an amount of 0.01 to 10 wt. % flocculant based on expected solid molecular sieve product yield, crystal size, and presence of nano particles and ionicity of the medium, preferably between 0.02 to 2 wt % flocculant based on expected solid molecular sieve product yield, crystal size, and presence of nano particles and ionicity of the medium, more preferably from 0.03 to 1.5 wt % based on expected solid molecular sieve product yield, crystal size, and presence of nano particles and ionicity of the medium. It is preferable that the product slurry and/or flocculant are diluted to obtain a volume of product slurry to volume of flocculant of between 1:1 and 10:1. Good mixing between the product slurry and the flocculant is also preferred. One can recover the flocculated sieve starting from the total mixture by centrifugation or filtration or one can allow the mixture to settle, decant the liquid, re-slurry with water, eventually repeatedly decant and re-slurry, and finally recover by centrifugation or filtration. The settling of the sieve can take from minutes to days; however, the settling can be accelerated by adding additional flocculant or use of high molecular weight flocculant. The flocculant is typically added to the slurry at room temperature, and is preferably added as a solution. Should a solid flocculant be used then it is preferable that a substantially homogeneous flocculant solution or suspension or emulsion is prepared by dissolving or dispersing the solid flocculant in a medium.

In one embodiment, a flocculent has an average molecular weight about 500 to about 50,000,000, preferably about 10,000 to about 20,000,000, more preferably about 20,000 to about 15,000,000, and most preferably about 50,000 to about 10,000,000.

The flocculant may be in solution, an emulsion, or a microemulsion, preferably an aqueous solution, emulsion, or micro-emulsion. Further, the flocculent in the aqueous solution may be diluted with water. Without being bound to any particular theory, it has been found that dilution of the molecular sieve slurry, preferably one recovered using a flocculent, prevents or reduces dissolution of the molecular sieve in the slurry. This benefit provides for a further improvement in yield, and allows for the slurry to be stored for an extended period of time.

A synthesis mixture comprising a molecular sieve and a flocculant has a pH depending on the composition of the molecular sieve, excess amount of template, degree of crystallization. In a preferred embodiment, the synthesis mixture has a pH in the range of from 2 to 10, preferably in the range of from 2.5 to 9.5, and most preferably in the range of from 3 to 9. Generally, the synthesis mixture is sealed in a vessel and heated, preferably under autogenous pressure, to a temperature in the range of about 80° C. to about 250° C., and more preferably about 150° C. to about 180° C. The time required to form the crystalline molecular sieve is typically from immediately up to several weeks, the duration of which is usually dependent on the temperature; the higher the temperature the shorter the duration. Typically, the crystalline molecular sieve product is formed, usually in a slurry state, and then a flocculant is introduced to this slurry, the synthesis mixture. The crystalline molecular sieve is then recovered by any standard technique well known in the art, for example centrifugation or filtration. Alternatively, in another embodiment, the flocculent is introduced into the synthesis mixture directly.

In one embodiment, the isolated or separated crystalline product, the synthesized molecular sieve, is washed, typically using a liquid such as water, from one to many times, or in a semi-continuous or continuous way for variable lengths of time. The washed crystalline product is then optionally dried, preferably in air, more preferably in flowing air, to a level such that the resulting, partially dried or dried crystalline product or synthesized molecular sieve has a LOI in the range of about 0.5 weight percent to about 80 weight percent, preferably the range is about greater than 1 weight percent to about 75 weight percent, more preferably about 5 weight percent to about 70 weight percent, even more preferably about 8 to about 65 weight percent, and most preferably about 10 weight percent to about 60 weight percent. This moisture containing crystalline product, synthesized molecular sieve or wet filtercake, is then used below in the formulation of the molecular sieve catalyst composition of the invention.

The amount of flocculant introduced to the reactor, or crystallization vessel, depends on the quantity of molecular sieve being recovered, the type of molecular sieve, the pH of the synthesis mixture, the size of the molecular sieve crystals, etc. In one embodiment, the amount of molecular sieve recovered is the range of about 50 kg to about 20,000 kg or greater, preferably in the range of from 100 kg to about 20,000 kg, more preferably about 150 kg to about 20,000 kg, and most preferably about 250 kg to about 20,000 kg. In another embodiment, the reactor vessel is capable of synthesizing an amount of molecular sieve in one batch or at one time in the range of about 50 kg to about 20,000 kg or greater, preferably greater than about 100 kg to about 20,000 kg, more preferably about 150 kg to about 20,000 kg, and most preferably about 250 kg to about 20,000 kg.

In one embodiment of the present invention, an over flocculated molecular sieve and, optionally, a phosphorous compound, preferably an acidic phosphorous compound, and/or, optionally, a non-over flocculated molecular sieve are combined to form a catalyst composition. In order to determine the extent of flocculation of a molecular sieve product recovered with a flocculation process, the following analytical method is followed by preparing a formulated slurry using the flocculated molecular sieve, which includes, but is not limited to, molecular sieves based on silicon, aluminum, and phosphorous; metal containing molecular sieves; and zeolites. The viscosity of the slurry is measured using a Brookfield DV-II+ Pro Viscometer (Brookfield Instrument Laboratories Inc., Middleboro, Mass.) using a #6 spindle at 10 RPM shear rate. The measurement is carried out at temperatures of 23-24° C. The viscometer is first calibrated with calibration standards having viscosities of 500 cPs, 1000 cPs, and 3000 cPs before taking a measurement of the slurry samples. These calibration standards are certified and are from Brookfield Instrument Laboratories Inc., Middleboro, Mass. The over-flocculated molecular sieve slurry, made according to the following procedure, has a viscosity at about 7,000 cPs or higher, while a non-over-flocculated molecular sieve slurry, made according to the following procedure, has a viscosity below 7,000 cPs.

A determination of the flocculation conditions of a sample of molecular sieve is made as follows. The slurry sample having a solids content of 45%, of which 45% being a molecular sieve, 13.5% alumina binder derived from aluminum chlorohydrite (ACH), and 41.5% kaolin clay is prepared by the following procedure. To make 1000 grams of formulated slurry: (1) add 244 grams of an aluminum chlorohydrite (ACH) solution from Reheis Inc., Berkeley Heights, N.J. (LOI: 75.1%) to 224.5 grams of de-ionized water and mix using a Yamato Model 2100 homogenizer (Yamato Scientific America Inc., Orangeburg, N.Y.) at 700 RPM for 5 minutes; (2) add 310 grams of flocculated molecular sieve and mix using Yamato mixer at 700 RPM for 10 minutes; then mix using a Silverson L4RT-A high-shear mixer (from Silverson Machines Inc., East Longmeadow, Mass.) at 6000 RPM for 3 minutes; (3) add 221.5 grams of APS Ultrafine clay from Engelhard Corporation, Gordon, Georgia (LOI: 15.69%) while mixing using Yamato mixer at 700 RPM for 10 minutes, then mix using a Silverson L4RT-A in-line mixer at 7500 RPM for 60 passes at a flow rate of 1500 g/min. The slurry is left to equilibrate at room temperature to 23-24° C. then the viscosity is measured. A molecular sieve that gives a slurry with a viscosity of about 7,000 cPs or higher prepared according to the procedure described above is defined herewith as an over-flocculated molecular sieve, and a molecular sieve that gives a slurry viscosity of less than 7,000 cPs is defined herewith as a non-over flocculated molecular sieve. A non-over flocculated molecular sieve includes, but is not limited to, a molecular sieve that has been recovered without the use of a flocculant.

For micro-crystalline materials recovered from a flocculation process, there are some debris deposited on the surface of the micro-crystalline materials. The debris is defined as material that is smaller in size and having a different composition than that of the micro-crystalline product. One way to express the amount of debris on a crystalline material is defined as surface coverage factor ($\Phi$), or debris factor, which is the fraction of the crystalline external surface covered by debris. An over flocculated molecular sieve, as used herein, may also have a debris factor, $\Phi$, greater than 0.2. An over flocculated molecular sieve may also give a spray dried product having an ARI greater than 1 wt. %/hr. A non-over flocculated molecular sieve, as used herein, may also have a debris factor, $\Phi$, less than 0.2, preferably less than 0.1. A non-over flocculated molecular sieve may also give a spray dried product having an ARI less than 1 wt. %/hr, more preferably less than 0.5 wt. %/hr. ARI, or Attrition Rate Index, is discussed further below.

In one embodiment of the present invention, the catalyst composition comprises an over flocculated molecular sieve recovered with a first flocculant and, optionally, a phosphorus compound, preferably an acidic phosphorous compound, and/or, optionally, a non-over flocculated molecular sieve is recovered with a second flocculant. The first flocculant and the second flocculant have an average molecular weight of about 500 to about 50,000,000, preferably about 10,000 to about 20,000,000, more preferably about 20,000 to about 15,000,000, most preferably about 30,000 to about 10,000,000. The amount of first flocculant used to recover the over flocculated molecular sieve is about 50 to about 100,000 ppm, preferably about 100 to about 50,000 ppm, more preferably about 200 to about 25,000 ppm. The amount of second flocculant used to recover the non-over flocculated molecular sieve is about 20 to about 50,000 ppm, preferably about 50 to about 30,000 ppm, more preferably about 100 to about 10,000 ppm. The first flocculant and the second flocculant may be the same.

In one embodiment of the present invention, the catalyst composition comprises about 5 wt % to about 95 wt % of an over flocculated molecular sieve, preferably about 10 wt % to about 90 wt % of an over flocculated molecular sieve, more preferably about 15 wt % to about 85 wt % of an over flocculated molecular sieve, most preferably about 20 wt % to about 80 wt % of an over flocculated molecular sieve. In one embodiment of the present invention, the catalyst composition comprises a phosphorous compound expressed in terms of $P_2O_5$ added during formulation in the range of about 0.03 wt % to about 20 wt % $P_2O_5$, preferably about 0.1 wt % to about 15 wt % $P_2O_5$, more preferably about 0.2 wt % to about 12 wt % $P_2O_5$, most preferably about 0.3 wt % to about 10 wt % $P_2O_5$. In one embodiment of the present invention, the catalyst composition comprises about 0 wt % to about 95 wt % of a non-over flocculated molecular sieve, preferably about 5 wt % to about 95 wt % of a non-over flocculated molecular sieve, more preferably about 10 wt % to about 90 wt % of a non-over flocculated molecular sieve, even more preferably about 15 wt % to about 85 wt % of a non-over flocculated molecular sieve, most preferably about 20 wt % to about 80 wt % of a non-over flocculated molecular sieve. The weight % are based on total weight of the molecular sieve(s) and phosphorous compound comprising the catalyst composition.

In one embodiment of the present invention, the catalyst composition has a weight ratio of the non-over flocculated molecular sieve to the over flocculated molecular sieve of about 1:20 to 20:1; preferably about 1:10 to 10:1; more preferably about 1:5 to 5:1.

In an embodiment of the present invention, the catalyst composition comprises about 5 wt % to about 100 wt % of an over flocculated molecular sieve, preferably about 10 wt % to about 95 wt % of an over flocculated molecular sieve, more preferably about 15 wt % to about 90 wt % of an over flocculated molecular sieve, yet more preferably about 20 wt % to about 85 wt %, most preferably about 25 wt % to about 80 wt % of an over flocculated molecular sieve, wherein the total weight percent is based on the total weight of the molecular sieve(s). In an embodiment of the present invention, the catalyst composition comprises about 0 wt % to about 95 wt % of a non-over flocculated molecular sieve, preferably about 5 wt % to about 90 wt % of a non-over flocculated molecular sieve, more preferably about 10 wt % to about 85 wt % of a non-over flocculated molecular sieve, even more preferably about 15 wt % to about 80 wt % of a non-over flocculated molecular sieve, most preferably about 20 wt % to about 75 wt % of a non-over flocculated molecular sieve, wherein the total weight percent is based on the total weight of the molecular sieve(s).

Method for Making Molecular Sieve Catalyst Compositions

Once the molecular sieve is synthesized and recovered as described above, depending on the requirements of the particular conversion process, the molecular sieve is then formulated into a molecular sieve catalyst composition, particularly for commercial use. The molecular sieves synthesized above are made or formulated into molecular sieve catalyst compositions by combining the recovered molecular sieve(s), with a binder, and optionally, but preferably, with a matrix material to form a formulated molecular sieve catalyst composition. It has been found that when thermally treating a synthesized molecular sieve having been recovered in the presence of a flocculant, prior to formulation, thermal treatment can maintain or improve the formulated molecular sieve catalyst composition's resistance to attrition in various conversion processes.

This formulated catalyst composition is formed into useful shape and sized particles by well-known techniques such as spray drying, pelletizing, extrusion, and the like, spray drying being the most preferred. It is also preferred that after spray drying for example that the formulated molecular sieve catalyst composition is then calcined.

Binder

There are many different binders that are useful in forming the molecular sieve catalyst composition. Non-limiting examples of binders that are useful alone or in combination include various types of hydrated alumina, silicas, and/or other inorganic oxide sol. One preferred alumina containing sol is aluminum chlorhydrate. The inorganic oxide sol acts like glue binding the synthesized molecular sieves and other materials such as the matrix together, particularly after thermal treatment. Upon heating, the inorganic oxide sol, preferably having a low viscosity, is converted into an inorganic oxide component. For example, an alumina sol will convert to an aluminum oxide following heat treatment.

Aluminum chlorhydrate, a hydroxylated aluminum based sol containing a chloride counter ion, has the general formula of $Al_mO_n(OH)_oCl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105-144 (1993), which is herein incorporated by reference. In another embodiment, the binders are alumina sols, predominantly comprising aluminum oxide, optionally including some silicon. In yet another embodiment, the binders are peptized alumina made by treating alumina hydrates such as pseudobohemite, with an acid, preferably an acid that does not contain a halogen, to prepare sols or aluminum ion solutions. Non-limiting examples of commercially available colloidal alumina sols include Nalco 8676 available from Nalco Chemical Co., Naperville, Ill., and Nyacol AL20DW, available from Nyacol Nano Technologies, Inc., Ashland, Mass.

In one embodiment, the weight ratio of the binder to the molecular sieve is in the range of about 0.1 to 0.5, more preferably in the range of from 0.11 to 0.48, even more preferably from 0.12 to about 0.45, yet even more preferably from 0.13 to less than 0.45, and most preferably in the range of from 0.15 to about 0.4. See for example U.S. Patent Application Publication No. U.S. 2003/0181322 published Sep. 25, 2003, which is herein fully incorporated by reference.

Matrix Material

The synthesized molecular sieves described above, in a preferred embodiment, is combined with a binder and one or more matrix material(s). Matrix materials are typically effective in reducing overall catalyst cost, act as thermal sinks assisting in shielding heat from the catalyst composition for example during regeneration, densifying the catalyst composition, increasing catalyst strength such as crush strength and attrition resistance, and to control the rate of conversion in a particular process.

Non-limiting examples of matrix materials include one or more of: rare earth metals, non-active, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. In one embodiment, the matrix material, preferably any of the clays, are subjected to well known modification processes such as calcination and/or acid treatment and/or chemical treatment. In one preferred embodiment, the matrix material is kaolin, particularly kaolin having an average particle size of about 0.1 µm to about 0.6 µm with a $d_{90}$ particle size of less than about 10 µm. Binder may also function as a matrix material. Where the binder functions as a matrix material, a second matrix material may also be added.

Upon combining the over flocculated molecular sieve, optionally a phosphorous compound, optionally a non-over flocculated molecular sieve, and the binder, with, optionally, a matrix material, in a liquid to form a slurry, mixing, preferably rigorous mixing, is needed to produce a substantially homogeneous mixture containing the flocculated molecular sieve. Non-limiting examples of suitable liquids include one or a combination of water, alcohol, ketones, aldehydes, and/or esters. The most preferred liquid is water. In one embodiment, the slurry is high shear or bead milled for a period of time sufficient to produce the desired slurry texture, particle size, and/or particle size distribution.

The liquid containing the over flocculated molecular sieve, optionally a phosphorous compound, optionally the non-over flocculated molecular sieve, and binder, and optionally the matrix material, are in the same or different liquid, and are combined in any order, together, simultaneously, sequentially, or a combination thereof. In the preferred embodiment, the same liquid, preferably water is used.

Solids Content

The molecular sieve catalyst composition in one embodiment is made by preparing a slurry containing a molecular sieve, a binder, and, optionally while preferably, a matrix material. The solids content of the preferred slurry includes about 20% to about 80% by weight of the molecular sieve, preferably about 25% to about 65% by weight of the molecular sieve, more preferably about 30% to about 50% by weight molecular sieve, about 5% to about 20%, preferably about 8% to about 15%, by weight of the binder, and about 30% to about 80%, preferably about 40% to about 60%, by weight of the matrix material.

In another embodiment, the solids content in a slurry comprising a molecular sieve, a binder, and optionally a matrix material, and a liquid medium is in the range of about 40 weight percent to about 80 weight percent, more preferably in the range of from 40.5 weight percent to about 70 weight percent, even more preferably in the range of from 41 weight percent to 60 weight percent, still even more preferably about 41.5 weight percent to about 59 weight percent, yet even more preferably in the range of from 42 weight percent to about 58 weight percent, and most preferably in the range of from 42.5 weight percent to about 57.5 weight percent.

The molecular sieve catalyst composition particles contains some water, templating agent or other liquid components, therefore, the weight percents that describe the solid content in the slurry are preferably expressed in terms exclusive of the amount of water, templating agent and removable components upon calcination at elevated temperature. The most preferred condition for measuring solids content is on a calcined basis as, for example, measured by the LOI procedure discussed below. On a calcined basis, the solid content in the slurry, more specifically, the molecular sieve catalyst composition particles in the slurry, are about 20 percent by weight to 80 percent by weight molecular sieve, 5 percent by weight to 20 percent by weight binder, and about 0 percent by weight to 80 percent by weight matrix material. See for example U.S. Pat. No. 6,787,501, which is herein fully incorporated by reference.

In another embodiment, the over flocculated molecular sieve, optionally a phosphorous compound, and optionally the non-over flocculated molecular sieve, are combined with a binder and/or a matrix material forming a slurry such that the pH of the slurry is above or below the isoelectric point (IEP) of the molecular sieve. Preferably the slurry comprises the molecular sieve, the binder and the matrix material and has a pH different from, above or below, preferably below, the IEP of the molecular sieve, the binder and the matrix material. In an embodiment, the pH of the slurry is in the range of from 2 to 7, preferably from 2.3 to 6.2; the IEP of the molecular sieve is in the range of about 2.5 to less than 7, preferably about 3.0 to 6.5; the IEP of the binder is greater than 10; and the IEP of the matrix material is less than about 3. See PCT Patent Publication WO 03/000412 A1 published Jan. 3, 2003, which is herein fully incorporated by reference.

Milling/Mixing

As the slurry is mixed, particle size reduction is achieved. It is preferable that these particles are small and have a desired size distribution such that the $d_{90}$ of these particles is less than 20 μm, preferably less than 15 μm, more preferably less than 10 μm, and most preferably about 7 μm. The $d_{90}$ for purposes of this patent application and appended claims means that 90 percent by volume of the particles in the slurry have a particle diameter lower than the $d_{90}$ value. For the purposes of this definition, the particle size distribution used to define the $d_{90}$ is measured using well known laser scattering techniques using a Microtrac Model S3000 particle size analyzer from Microtrac, Inc., Largo, Fla.

In an embodiment, the invention relates to a catalyst slurry that comprises (a) an over flocculated molecular sieve; (b) a binder; and (c) optionally a matrix material. In another embodiment of the present invention, the catalyst slurry has a viscosity less than about 10,000 cPs at 10 RPM, preferably less than about 7,000 cPs at 10 RPM. In another embodiment of the present invention, the catalyst slurry has a solids content greater than about 40%. In another embodiment, the catalyst slurry further comprises a second flocculated molecular sieve having a slurry viscosity of at least 1,000 cPs measured at 10 RPM less than the one over flocculated molecular sieve. In an embodiment, the invention relates to a catalyst slurry wherein the second flocculated molecular sieve comprises a non-over flocculated molecular sieve. In another embodiment, the catalyst slurry further comprises a phosphorous compound, preferably an acidic phosphorous compound. In another embodiment of the present invention, an activated molecular sieve catalyst composition that has an ARI of less than about 1.0 weight %/hr, preferably less than 0.60 weight %/hr., preferably less than 0.50 weight %/hr., is formed by: (a) mixing the catalyst slurry to form a formulation composition; (b) forming the formulation composition in a forming unit to form a shaped catalyst; and (c) calcining the shaped catalyst to form the activated molecular sieve catalyst composition.

In one embodiment, the slurry of the over flocculated molecular sieve, optionally, a phosphorous compound, optionally the non-over flocculated molecular sieve, binder and optionally the matrix material is mixed or milled to achieve a sufficiently uniform slurry of particles of the molecular sieve catalyst composition to form a formulation composition that is then fed to a forming unit that produces the molecular sieve catalyst composition or formulated molecular sieve catalyst composition.

As stated above, the over flocculated molecular sieve and, optionally, the non-over flocculated molecular sieve are mixed with a binder, optionally a phosphorous compound, and optionally a matrix material, as well as a liquid solvent component, to form a slurry. The components can be mixed in any order, and the mixture is thoroughly stirred to form the slurry. The more thorough the stirring, the better the consistency of the slurry, and the more uniform will be the dried catalyst composition.

The over flocculated molecular sieve, optionally, the non-over flocculated molecular sieve, binder, optionally a phosphorous compound, and optionally a matrix material, are mixed together at a breakage energy effective to break apart agglomerates and aggregates, as defined in *Practical Dispersion*, R. F. Conley, VCH, New York, p. 213, 1996, which is incorporated herein by reference. Mixers capable of mixing together components at the appropriate breakage energy include impeller mills, ball mills, stirred media mills, vibratory mills, multiple roll mills and ultrasonic dispersion devices. Further description of appropriate mixing equipment is described in *Solid-Liquid Dispersions*, B. Dobias et al., pp. 22-27, Marcel Dekker, New York, 1999, which is incorporated herein by reference.

In one embodiment, over flocculated molecular sieve, optionally, the non-over flocculated molecular sieve, binder, optionally a phosphorous compound, and optionally a matrix material are mixed together at the appropriate breakage energy using a bead mill. Preferably, the bead mill incorporates beads in the mixing portion of the mixer having a relative span factor (RSF) that is relatively low, meaning that there is small variation in bead diameter. The RSF is calculated as $RSF=(d_{90}-d_{10})/d_{50}$, wherein $d_{90}$ refers to particle diameter at 90% particle distribution, $d_{10}$ refers to particle diameter at 10% particle distribution, and $d_{50}$ refers to particle diameter at 50% particle distribution. Preferably, the beads have a RSF of not greater than 0.2, more preferably not greater than 0.15, and most preferably not greater than 0.1.

In one embodiment, the components used to make the molecular sieve catalyst composition are mixed at breakage energy of at least $10^{-5}$ cal cm$^{-2}$. Preferably, the components used to make the molecular sieve catalyst composition are mixed at breakage energy of at least $5 \times 10^{-4}$ cal cm$^{-2}$, and more preferably at least $10^{-4}$ cal cm$^{-2}$.

The breakage energy should be high enough to obtain the desired characteristics of the invention. However, the breakage energy should not be so high as to break apart chemical bonds. In another embodiment, the components used to make the molecular sieve catalyst composition are mixed at breakage energy of not greater than $10^{-1}$ cal cm$^{-2}$. Preferably, the components used to make the molecular sieve catalyst composition are mixed at breakage energy of not greater than $6 \times 10^{-2}$ cal cm$^{-2}$, and more preferably not greater than $5 \times 10^{-2}$ cal cm$^{-2}$. Bead mills typically generate a breakage energy of $6 \times 10^{-5}$ to $6 \times 10^{-2}$ cal cm$^{-2}$, whereas impeller mills typically generate a breakage energy of $10^{-5}$ to $2 \times 10^{-4}$ cal cm$^{-2}$, and ball mills generate a breakage energy of $10^{-5}$ to $6 \times 10^{-3}$ cal cm$^{2}$.

Forming/Shaping

In a preferred embodiment, the forming unit is a spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray dryer is used as the forming unit, typically, any one or a combination of the slurries described above, more particularly a slurry of the over flocculated molecular sieve, phosphorous compound, optionally the non-over flocculated molecular sieve, binder, and optionally matrix material is co-fed to the spray dryer with a drying gas with an average inlet temperature ranging from 200° C. to 550° C., and a combined outlet temperature ranging from 70° C. to about 225° C. In an embodiment, the average diameter of the spray dried formed catalyst composition is about 40 μm to about 300 μm, preferably about 45 μm to about 250 μm, more preferably about 50 μm to about 200 μm, and most preferably about 55 μm to about 120 μm.

During spray drying, the slurry is passed through a nozzle distributing the slurry into small droplets, resembling an aerosol spray into a drying chamber. Atomization is achieved by forcing the slurry through a single nozzle or multiple nozzles with a pressure drop in the range of from 100 psia to 1000 psia (690 kPaa to 6895 kPaa). In another embodiment, the slurry is co-fed through a single nozzle or multiple nozzles along with an atomization fluid such as air, steam, flue gas, or any other suitable gas. Generally, the size of the microspheres is controlled to some extent by the solids content of the slurry. However, control of the size of the catalyst composition and its spherical characteristics are controllable by varying the slurry feed properties and conditions of atomization, such as nozzle size, atomization medium, pressure drop, and flow rate.

Other methods for forming a molecular sieve catalyst composition are described in U.S. Pat. No. 6,509,290 (spray drying using a recycled molecular sieve catalyst composition), which is herein incorporated by reference.

In a preferred embodiment, once the molecular sieve catalyst composition is formed, to further harden and/or activate the formed catalyst composition, the spray dried molecular sieve catalyst composition or formulated molecular sieve catalyst composition is calcined. Typical calcination temperatures are in the range of about 500° C. to about 800° C., and preferably about 550° C. to about 700° C., preferably in a calcination environment such as air, nitrogen, helium, flue gas (combustion product lean in oxygen), or any combination thereof. Calcination time is typically dependent on the degree of hardening of the molecular sieve catalyst composition and is in the range of about 15 minutes to about 20 hours at a temperature in the range of from 500° C. to 700° C.

In one embodiment, the molecular sieve catalyst composition or formulated molecular sieve catalyst composition has an ARI less than 10 weight percent per hour, preferably less than 5 weight percent per hour, more preferably less than 2 weight percent per hour, and most preferably less than 1 weight percent per hour. ARI was calculated as discussed below.

Process for Using the Molecular Sieve Catalyst Compositions

The molecular sieve catalyst compositions described above are useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

The molecular sieve catalyst compositions described above are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In an embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene and/or propylene. Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition of the invention into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The are many processes used to convert feedstock into olefin(s) including various cracking processes such as steam cracking, thermal regenerative cracking, fluidized bed cracking, fluid catalytic cracking, deep catalytic cracking, and visbreaking. The most preferred process is generally referred to as gas-to-olefins (GTO) or alternatively, oxygenate-to-olefins (OTO) or methanol-to-olefins (MTO). In a MTO or an OTO process, typically an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. No. 4,076,796, U.S. Pat. No. 6,287,522 (dual riser), and *Fluidization Engineering*, D. Kunii and O. Levenspiel, Robert E. Krieger Publishing Company, New York, N.Y. 1977, which are all herein fully incorporated by reference. The preferred reactor type are riser reactors generally described in Riser Reactor, *Fluidization and Fluid-Particle Systems*, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In the preferred embodiment, a fluidized bed process or high velocity fluidized bed process includes a reactor system, a regeneration system and a recovery system.

Reactor System

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition or coked version thereof is introduced. In one embodiment, the molecular sieve catalyst composition or coked version thereof is contacted with a liquid or gas, or combination thereof, prior to being introduced to the riser reactor(s), preferably the liquid is water or methanol, and the gas is an inert gas such as nitrogen.

The feedstock entering the reactor system is preferably converted, partially or fully, in the first reactor zone into a gaseous effluent that enters the disengaging vessel along with a coked or further coked molecular sieve catalyst composition. In the preferred embodiment, cyclone(s) within the disengaging vessel are designed to separate the molecular sieve catalyst composition, preferably a coked or further coked molecular sieve catalyst composition, from the gaseous effluent containing one or more olefin(s) within the disengaging zone. Cyclones are preferred, however, gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel, typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel.

The conversion temperature employed in the conversion process, specifically within the reactor system, is in the range of about 200° C. to about 1000° C., preferably about 250° C. to about 800° C., more preferably about 250° C. to about 750° C., yet more preferably about 300° C. to about 650° C., yet even more preferably about 350° C. to about 600° C., and most preferably about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of about 0.1 kPaa to about 5 MPaa, preferably about 5 kPaa to about 1 MPaa, and most preferably about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor. Typically, the WHSV is in the range of about 1 $hr^{-1}$ to about 5000 $hr^{-1}$, preferably about 2 $hr^{-1}$ to about 3000 $hr^{-1}$, more preferably about 5 $hr^{-1}$ to about 1500 $hr^{-1}$, and most preferably about 10 $hr^{-1}$ to about 1000 $hr^{-1}$. In one preferred embodiment, the WHSV is greater than 20 $hr^{-1}$, preferably the WHSV for conversion of a feedstock containing methanol and dimethyl ether is in the range of about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. Pat. No. 6,552,240, which is herein incorporated by reference. Other processes for converting an oxygenate to olefin(s) are described in U.S. Pat. No. 5,952,538 (WHSV of at least 20 $hr^{-1}$ and a Temperature Corrected Normalized Methane Selectivity (TCNMS) of less than 0.016), EP-0 642 485 B1 (WHSV is from 0.01 $hr^{-1}$ to about 100 $hr^{-1}$, at a temperature of about 350° C. to 550° C.), and PCT WO 01/23500 published Apr. 5, 2001 (propane reduction at an average catalyst feedstock exposure of at least 1.0), which are all herein fully incorporated by reference.

The coked molecular sieve catalyst composition is withdrawn from the disengaging vessel, preferably by one or more cyclones(s), and introduced to the regeneration system.

Regeneration System

The regeneration system comprises a regenerator where the coked catalyst composition is contacted with a regeneration medium, preferably a gas containing oxygen, under general regeneration conditions of temperature, pressure and residence time. Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition. By controlling the flow of the regenerated molecular sieve catalyst composition or cooled regenerated molecular sieve catalyst composition from the regeneration system to the reactor system, the optimum level of coke on the molecular sieve catalyst composition entering the reactor is maintained. There are many techniques for controlling the flow of a molecular sieve catalyst composition described in Michael Louge, *Experimental Techniques, Circulating Fluidized Beds*, Grace, Avidan and Knowlton, eds., Blackie, 1997 (336-337), which is herein incorporated by reference.

The regeneration temperature is in the range of about 200° C. to about 1500° C., preferably about 300° C. to about 1000° C., more preferably about 450° C. to about 750° C., and most preferably about 550° C. to 700° C. The regeneration pressure is in the range of about 15 psia (103 kPaa) to about 500 psia (3448 kPaa), preferably about 20 psia (138 kPaa) to about 250 psia (1724 kPaa), more preferably about 25 psia (172 kPaa) to about 150 psia (1034 kPaa), and most preferably about 30 psia (207 kPaa) to about 60 psia (414 kPaa). The preferred residence time of the molecular sieve catalyst composition in the regenerator is in the range of about one minute to several hours, most preferably about one minute to 100 minutes, and the preferred volume of oxygen in the gas is in the range of about 0.01 mole percent to about 5 mole percent based on the total volume of the gas.

Other regeneration processes are described in U.S. Pat. No. 6,023,005 (coke levels on regenerated catalyst), U.S. Pat. No. 6,245,703 (fresh molecular sieve added to regenerator) and U.S. Pat. No. 6,290,916 (controlling moisture), U.S. Pat. No. 6,613,950 (cooled regenerated catalyst returned to regenerator), U.S. Pat. No. 6,441,262 (regenerated catalyst contacted with alcohol), and PCT WO 00/49106 published Aug. 24, 2000 (cooled regenerated catalyst contacted with by-products), which are all herein fully incorporated by reference.

The gaseous effluent is withdrawn from the disengaging system and is passed through a recovery system.

Recovery System

There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like. Non-limiting examples of these towers, columns, splitters or trains used alone or in combination include one or more of a demethanizer, preferably a high temperature demethanizer, a dethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

In particular with a conversion process of oxygenates into olefin(s) utilizing a molecular sieve catalyst composition the resulting effluent gas typically comprises a majority of ethylene and/or propylene and a minor amount of four carbon and higher carbon number products and other by-products, excluding water. In one embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system to remove various non-limiting examples of contaminants and by-products including, but not limited to, generally polar compounds such as water, alcohols, carboxylic acids, ethers, carbon oxides, ammonia and other nitrogen compounds, chlorides, hydrogen and hydrocarbons such as acetylene, methyl acetylene, propadiene, butadiene and butyne.

Other recovery systems that include purification systems, for example for the purification of olefin(s), are described in *Kirk-Othmer Encyclopedia of Chemical Technology, 4th Edition*, Volume 9, John Wiley & Sons, 1996, pages 249-271 and 894-899, which is herein incorporated by reference. Purification systems are also described in for example, U.S. Pat. No. 6,271,428 (purification of a diolefin hydrocarbon stream), U.S. Pat. No. 6,293,999 (separating propylene from propane), and U.S. Pat. No. 6,593,506 (purge stream using hydrating catalyst), which is herein incorporated by reference.

Included in the recovery systems of the invention are reaction systems for converting the products contained within the effluent gas withdrawn from the reactor or converting those products produced as a result of the recovery system utilized. Suitable well known reaction systems as part of the recovery system primarily take lower value products such as the $C_4$ hydrocarbons, butene-1 and butene-2 and convert them to higher value products. Non-limiting examples of these types of reaction systems include U.S. Pat. No. 5,955,640 (converting a four carbon product into butene-1), U.S. Pat. No. 4,774,375 (isobutane and butene-2 oligomerized to an alkylate gasoline), U.S. Pat. No. 6,049,017 (dimerization of n-butylene), U.S. Pat. Nos. 4,287,369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., *Process for Upgrading $C_3$, $C_4$ and $C_5$ Olefinic Streams*, Pet. & Coal, Vol. 37, No. 4 (1995) (dimerizing or oligomerizing propylene, butylene and pentylene), which are all herein fully incorporated by reference.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in effluent gas fed to another reactor) PCT WO 01/60770 published Aug. 23, 2001 and U.S. Pat. No. 6,441,261 (high pressure), U.S. patent application Ser. No. 09/507,838 filed Feb. 22, 2000 (staged feedstock injection), and U.S. Pat. No. 6,518,475 (acetone co-fed), which are all herein fully incorporated by reference.

Integrated Processes

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of about 700° C. to about 1200° C. and syngas pressures are in the range of about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas. Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of about 150° C. to about 450° C. and at a synthesis pressure in the range of about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through well known purification processes, distillation, separation and fractionation, resulting in a purified oxygenate containing stream, for example, commercial Grade A and AA methanol. The oxygenate containing stream or purified oxygenate containing stream, optionally with one or more diluents, is contacted with one or more molecular sieve catalyst compositions described above in any one of the processes described above to produce a variety of prime products, particularly light olefin(s), ethylene and/or propylene. Non-limiting examples of this integrated process is described in EP-B-0 933 345, which is herein fully incorporated by reference. In another more fully integrated process, optionally with the integrated processes described above, olefin(s) produced are directed to, in one embodiment, one or more polymerization processes for producing various polyolefins. (See for example U.S. patent application Ser. No. 09/615,376 filed Jul. 13, 2000, which is herein fully incorporated by reference.)

Light Olefin Usage

The light olefin products, especially the ethylene and the propylene, are useful in polymerization processes that include solution, gas phase, slurry phase and high pressure processes, or a combinations thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

In an embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

In addition to polyolefins, numerous other olefin derived products are formed from the olefin(s) recovered by any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

EXAMPLES

Test Methods

Determination of the percentage of liquid or liquid medium and the percentage of template for purposes of this patent specification and appended claims uses a Thermal Gravimetric Analysis (TGA) technique as follows: An amount of a molecular sieve material, the sample, is loaded into a sample pan of a Cahn TG-121 Microbalance, available from Cahn Instrument, Inc., Cerritos, Calif. During the TGA technique, a flow of 114 cc/min (STP) air was used. The sample is then heated from 25° C. to 180° C. at 30° C./min, held at 180° C. for 3 hours or until the weight of this sample becomes constant. The weight loss is defined as the Loss on Drying (LOD) and represents the fraction of the original sample that is principally water or other liquid medium. Subsequently, the sample is heated at 30° C./min from 180° C. to 650° C. and held at 650° C. for 2 hours. This second loss in weight is considered to be due to removing the template contained in the sieve crystals. The sum of these two losses relative to the initial sample weight is defined as the Loss-On-Ignition (LOI).

The attrition resistance of a molecular sieve catalyst composition is measured using an Attrition Rate Index (ARI), measured in weight percent catalyst composition attrited per hour. ARI is measured by adding 6.0 g of catalyst composition having a particle size distribution ranging from 53 microns to 125 microns to a hardened steel attrition cup. Approximately 23,700 cc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent the catalyst composition that has broken apart through attrition. The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst in grams charged to the attrition cup expressed on per hour basis is the ARI, in weight percent per hour (wt. %/hr). ARI is represented by the formula: ARI=C/(B+C)/D multiplied by 100%, wherein B is weight of catalyst composition left in the cup after the attrition test, C is the weight of collected fine catalyst particles after the first hour of attrition treatment, and D is the duration of treatment in hours after the first hour attrition treatment.

Viscosity measurement of catalyst formulation slurries was conducted using a Brookfield DV-II+PRO viscometer (Brookfield Instrument Laboratories Inc., Middleboro, Mass.) using a #6 spindle at a variety of shear rate, ranging, for example, from 10 RPM to 100 RPM. All measurements were carried out at room temperature. The viscometer was first calibrated with calibration standards having viscosities of 500 cps, 1000 cps, and 3000 cps before measuring the slurry samples. These calibration standards were certified from Brookfield Instrument Laboratories Inc., Middleboro, Mass.

Apparent bulk density (ABD) of a catalyst was determined by first weighing a KIMAX graduated cylinder from KAMBLE USA, accurate to 0.1 cc of 25 cc capacity, and the cylinder weight $W_a$, was recorded. Approximately 25 cc of a spray dried and calcined catalyst was poured into the graduated cylinder, the cylinder bottom was tapped against a lab bench surface at a frequency of 160-170 times per minute for 30 sec to pack the catalyst in the cylinder. The final weight of the cylinder containing the catalyst, $W_b$, was recorded, and the volume of the catalyst, $V_c$, was also recorded. ABD is calculated as ABD=$(W_b-W_a)/V_c$ in gram per cc.

Micropore surface area (MSA) is a measurement of the amount of micropores present in a porous material. It is defined as the difference between the total surface area-BET surface area, determined from whatever relative pressures are required to give a linear plot, and the external surface area, calculated from the slope of the linear region of the t-plot, with a small correction to put it on the same basis as the BET surface area. This technique is more sensitive than X-ray diffraction for measuring zeolite or molecular sieve content quantity in many cases, particularly, for composite catalysts, consisting of a zeolite or molecular sieve, a binder, and a filler. This approach has been used for determining the amount of zeolite in cracking catalyst by Johnson [M. F. L. Johnson, J. Catal., 52, 425-431 (1978)].

The t-plot is a transformation of the adsorption isotherm in which relative pressure is replaced by t, the statistical thickness of the adsorbed layer on nonporous material at the corresponding relative pressure. It was first proposed by Lippens and de Boer for dertermining various characteristics of pores systems, such as pore shapes [B. C. Lippens, and J. H. de Boer, J. Catal., 4, 319 (1965)].

Sing [K. S. W. Sing, Chem. Ind., 829 (1967)] has introduced that the extrapolation of a linear t-plot to t=0 can yield the volume of micropores. To determine the MSA, a MICROMERITICS Gemini 2375 from Micromeritics Instrument Corporation, Norcross, Ga. was used. An amount of catalyst, 0.15 g-0.6 g, was loaded into the sample cell for degassing at 300° C. for a minimum of 2 hours. During the analysis, the Evacuation Time was 1.0 minute, No Free Space was used, and Sample Density of 1.0 was used. There were a total of 13 adsorption data points ($p/p_o$) collected with adsorption targets of 0.00500, 0.07500, 0.01000, 0.05000, 0.10000, 0.15000, 0.20000, 0.25000, 0.30000, 0.40000, 0.60000, 0.75000, and 0.95000. The correction factor used in the t-plot was 0.975 $p/p_o$. There were no desorption points collected. Other analysis parameters included, Analysis Mode: Equilibrate; Equilibration Time: 5 seconds; Scan Rate: 10 seconds. A t-plot from $p/p_o$ of 0.000000 to 0.900000 was constructed using the ASTM certified form of the Harkins and Jura equation (H-J Model):

$$t(p)=(13.99/(0.034-\log(p/p_o)))^{0.5}$$

It has been shown by Cape and Kibby [J. A. Cape and C. L. Kibby, J. Colloids and Interface Science, 138, 516-520 (1990)] that the conventional BET surface area of a microporous material can be decomposed quantitatively, as expressed by the equation given below:

$$S_{micro} = S_{tot} - S_{ext} = \upsilon_m / d_j$$

where $\upsilon_m$ is the micropore volume, $S_{micro}$ is the micropore area calculated from $S_{tot}$ and $S_{ext}$. $S_{tot}$ is given by the conventional BET method, and $S_{ext}$ is the external area taken from the t-plot. $d_j$ is a nonphysical length the value of which depends on the pressure used in the experiments. The proportionality factor, $d_j$, was determined quantitatively by the pressures used in the BET fits.

To determine the debris factor, a scanning electron microscope (SEM) was used. For micro-crystalline materials (molecular sieves and zeolites) recovered from a flocculation process, there are some debris deposited on the surface of the micro-crystalline materials. The debris is defined as material that is smaller in size and having a different composition than that of the micro-crystalline product. One way to express the amount of debris on a crystalline material is defined as surface coverage factor ($\Phi$), or debris factor, which is the fraction of the crystalline external surface covered by debris. A convenient way to estimate the debris factor is to use scanning electron microscopy (SEM). This can be done by directly measuring the projected area of the debris on all sides of a crystal under imaging conditions or by taking a SEM image at magnifications of 5,000 to 50,000 times and then estimating the area covered by debris. A debris factor of zero means that the crystal surface is free of any debris. A debris factor of one means that the crystalline external surface is fully covered by debris. The smaller the debris factor the less debris on the crystal surface.

In order to provide a better understanding of the present invention including representative advantages thereof, the following examples are offered.

Example 1

Example 1 slurry was prepared by (1) adding 202.5 g of an aluminum chlorohydrite (ACH) solution from Reheis Inc., Berkeley Heights, N.J. (LOI: 76%) to 110.5 g of de-ionized water and mixed using a Yamato Model 2100 homogenizer (Yamato Scientific America Inc., Orangeburg, N.Y.) at 700 RPM for 5 minutes resulting in a mixture having a pH of 3.62 at 23.4° C.; (2) adding 310.9 g of AEI/CHA SAPO intergrowth non-over flocculated molecular sieve having a debris factor of 0.09 (LOI: 47.90%) and mixing using Yamato mixer at 700 RPM for 10 minutes, giving a slurry having a pH of 3.66 at 23.7° C.; then mixed using a Silverson L4RT-A high-shear mixer at 6000 RPM for 3 minutes, giving a slurry having pH of 3.53 at 30.8° C.; (3) adding 176 g of Hydrite UF kaolin clay from Imerys, Rosswell, Ga. (LOI: 15.13%) while mixing using Yamato mixer at 700 RPM for 10 minutes, producing a slurry having a pH of 3.56 at 29.8° C., then mixing using a Silverson L4RT-A high-shear mixer at 6000 RPM for 3 minutes, giving a slurry having pH of 3.48 at 34.2° C.; (4) milling the slurry from step (3) by passing it through an Eiger Mini Mill 250 (from Eiger Machinery Inc., Gray Lake, Ill.) at 3000 RPM for a single pass, giving a slurry having pH of 3.70 at 23° C. The resulting slurry had a 45.31% solids content, 45% sieve, 13.5% alumina binder, and 41.5% clay, and a viscosity of 4800 cps measured using a Brookfield DV-II+PRO Viscometer, number 6 spindle at 10 rpm. An amount of 500-750 g of the slurry was spray dried. The spray dryer operated in a down spray mode using an atomization nozzle of 1 mm. The spray drying conditions were: feed rate: 30.8 g/min; inlet temperature: 350° C.; atomization pressure: 1 bar; carrier gas (nitrogen) flow at 60% of full setting. Spray dried products were collected in a cyclone. They were calcined in a muffle furnace at 650° C. in air for 2 hours. The calcined samples were used for attrition and particle size analysis. The resulting catalyst gave an ARI of 0.57%/hr, an ABD of 0.81 g/cc, and a micropore surface area of 224.4 m²/g.

Example 2

Example 2 slurry was prepared by (1) adding 202.5 g of aluminum chlorohydrate solution (LOI: 76%) from Reheis chemical Inc., Berkeley Heights, N.J., to 103.9 g of de-ionized water mixed using a Yamato Model 2100 homogenizer (Yamato Scientific America Inc., Orangeburg, N.Y.) at 700 RPM for 5 minutes giving a solution having a pH of 3.01 at 23° C.; (2) adding 317.5 g of AEI/CHA SAPO intergrowth over flocculated molecular sieve having a debris factor of 0.23 (LOI: 48.98%) and mixing using Yamato mixer at 700 RPM for 10 minutes, resulting in a slurry having a pH of 3.12 at 23° C.; then milling using a Silverson L4RT-A high-shear mixer (Silverson Machines Inc., East Longmeadow, Mass.) at 6000 RPM for 3 minutes, giving a slurry having pH of 2.90 at 30.4° C.; (3) adding Hydrite UF kaolin clay from Imerys, Rosswell, Ga. (LOI: 15.13%) while mixing using Yamato mixer at 700 RPM, when a small amount of clay was added it led to a pate-like product too thick to process, water was added in order to make the 176 g of clay into the slurry and to produce a slurry that could be processed. It was mixed for 10 minutes, producing a slurry having a pH of 3.14 at 25.9° C., then mixing using a Silverson L4RT-A high-shear mixer at 6000 RPM for 3 minutes, giving a slurry having pH of 3.06 at 30° C.; (4) milling the slurry from step (3) by passing it through a Eiger Mini Mill 250 (from Eiger Machinery Inc., Gray Lake, Ill.) at 3000 RPM for a single pass, giving a slurry having pH of 3.65 at 23° C. This led to a slurry with 39.8% solids content, 45% sieve, 13.5% alumina binder, and 41.5% clay, and a viscosity of 8400 cPs measured using a Brookfiled DV-II+ PRO Viscometer, number 6 spindle at 10 rpm. An amount of 500-750 g of the slurry was spray dried. The spray dryer operated in a down spray mode using an atomization nozzle of 1 mm. The spray drying conditions were: feed rate: 40 g/min; inlet temperature: 350° C.; atomization pressure: 1 bar; carrier gas (nitrogen) flow at 60% of full setting. Spray dried products were collected in a cyclone. They were calcined in a muffle furnace at 650° C. in air for 2 hours. The calcined samples were used for attrition and particle size analysis. The resulting catalyst gave an ARI of 1.34%/hr, an ABD of 0.76 g/cc, and a micropore surface area of 218.9 m²/g.

Example 3

Example 3 slurry containing approximately 44 wt % solids was prepared according to this procedure: (A) adding 27.3 g of phosphorus acid (Aldrich Chemical, Milwakee, Wis.) to 259.1 g of deionized water and mixing at 700 rpm for 5 minutes using a Yamato Model 2100 homogenizer (Yamato Scientific America Inc., Orangeburg, N.Y.) to give a solution having pH of 0.27 at 20.8° C.; (B) adding 506.3 g of aluminum chlorohydrate solution (LOI: 76%) (ACH, from Reheis Inc., Berkeley Heights, N.J.) to the solution obtained in step (A) mixing at 700 RPM for 10 minutes using the Yamato homogenizer Model 2100 used in step (A), obtaining a solution having a pH of 2.38 measured at 29° C.; (C) adding 793.8 g of a AEI/CHA SAPO intergrowth over flocculated molecular sieve having a debris factor of 0.23 (LOI: 48.98%) to the solution from step (B) and mixing at 700 RPM for 10 minutes using the Yamato homogenizer Model 2100 used in step (A), a slurry was thus obtained having a pH of 2.66 measured at 26.6° C.; (D) the slurry from step (C) was treated using a Silverson high shear mixer at 6000 RPM for 3 minutes, resulting in a slurry having pH of 2.63 at 30.7° C.; (E) adding 413.6 g of Hydrite Ultrafine kaolin clay (LOI: 15.13%, Imerys, Roswell, Ga.) under mixing at 700 RPM for 10 minutes using the Yamato homogenizer Model 2100 used in step (A). This thick slurry was transferred to an Eiger bead mill Model M250 (Eiger Machinery, Inc., Grayslake, Ill.) having a ceramic chamber and using high density and high purity yttria-stabilized zirconia microbeads of 0.65 mm in size at 3000 RPM for a single pass, the slurry produced had a pH of 3.67 measured at 23° C. for one pass. This milled slurry was measured to contain 44 wt % solids, of which 45% is sieve, 13.5% $Al_2O_3$, 2.5% $P_2O_5$, and 39% clay, and gave a pH of 2.85 measured at 23.5° C. The viscosity of the slurry was measured to be 3,700 cPs at 10 RPM using a Brookfield Viscometer, Model DV-II+PRO, spindle number 6 (see also Table 1 for additional viscosities at other rotation rates). 450 g of the milled slurry was spray dried using a Yamato DL-41 spray dryer (Yamato Scientific America, Orangeburg, N.Y.). The spray dryer operated in a down spray mode using an air atomization nozzle with an aperature of 1 mm. The spray drying conditions were: inlet temperature: 350° C.; atomization pressure: 1 bar; carrier gas (nitrogen) flow at 60% of full setting. Slurry was delivered to the spray dryer by a Master-Flex S/L pump using a setting of 50 rpm. Spray dried products were collected in a cyclone. They were calcined in a muffle furnace at 650° C. in air for 2 hours. The spray dried and calcined catalyst was measured to have an ABD of 0.85 g/cc and a micropore surface area of 219.2 $m^2$/g. The resulting catalyst had an ARI of 0.22%/hr.

thick slurry, having 44% solids content, 45% sieve, 13.5% alumina binder, and 39% clay and 2.5% $P_2O_5$ derived from $H_3PO_3$. This slurry was milled using a Silverson L4RT-A in-line mixer at 7500 RPM for 75 minutes operated in a circulation mode. The viscosity of the slurry was measured at 10 RPM using a Brookfield Viscometer, Model DV-II+PRO, spindle number 6. Properties of the slurry are given in Table 2. The slurry was spray dried using a Yamato DL-41 spray dryer (Yamato Scientific America, Orangeburg, N.Y.). An amount of 500-750 g of the slurry was spray dried. The spray dryer operated in a down spray mode using an atomization nozzle of 1 mm. The spray drying conditions were: feed rate: 40 g/min; inlet temperature: 350° C.; atomization pressure: 1 bar; carrier gas (nitrogen) flow at 60% of full setting. Spray dried products were collected in a cyclone. They were calcined in a muffle furnace at 650° C. in air for 2 hours. The resulting catalyst had an ARI of 0.49%/hr.

Example 5

Example 5 slurry was prepared by (1) adding 28.2 g of phosphorus acid (LOI: 17.5%, Aldrich Chemical, Milwaukee, Wis.) to 342.1 g of de-ionized water and mixing using a Yamato Model 2100 homogenizer (Yamato Scientific America Inc., Orangeburg, N.Y.) at 700 RPM for 10 minutes; (2) adding 523.1 g of aluminum chlorohydrate solution from Reheis chemical Inc., Berkeley Heights, N.J., by mixing using a Yamato Model 2100 homogenizer (Yamato Scientific America Inc., Orangeburg, N.Y.) at 700 RPM for 10 minutes; (3) adding 326.8 g of AEI/CHA SAPO intergrowth non-over flocculated molecular sieve having a debris factor of 0.09 (LOI: 35.97%) and mixing using Yamato mixer at 700 RPM for 5 minutes then adding 352.4 g of AEVCHA SAPO inter-

TABLE 1

Properties of Slurries Prepared Using a Bead Mill Mixer Used in Examples 1, 2, and 3

| | | | Other Slurry Properties | | | | | | | | | |
|---|---|---|---|---|---|---|---|---|---|---|---|---|
| Ex. | Solids | Sieve | | Clay | $P_2O_5$ | pH of | Viscosity (cPs) at Different Shear Rate (RPM) | | | | | |
| # | Content wt % | wt % | ACH-$Al_2O_3$ | % | % | Slurry | 100 | 60 | 30 | 20 | 10 | 6 |
| 1 | 45.31 | 45 | 13.5 | 41.5 | 0 | 3.67 | 840 | 1200 | 2033 | 2850 | 4800 | 7000 |
| 2 | 39.8 | 45 | 13.5 | 41.5 | 0 | 3.65 | 1190 | 1817 | 3200 | 4800 | 8400 | 13167 |
| 3 | 44 | 45 | 13.5 | 39 | 2.5 | 2.65 | 720 | 983.3 | 1600 | 2200 | 3700 | 5333 |

Example 4

Example 4 slurry was prepared by (1) adding 26.7 g of phosphorus acid (LOI: 17.5%, Aldrich Chemical, Milwaukee, Wis.) to 297.8 g of de-ionized water and mixing using a Yamato Model 2100 homogenizer (Yamato Scientific America Inc., Orangeburg, N.Y.) at 700 RPM for 10 minutes; (2) adding 495 g of aluminum chlorohydrate solution from Reheis chemical Inc., Berkeley Heights, N.J., by mixing using a Yamato Model 2100 homogenizer (Yamato Scientific America Inc., Orangeburg, N.Y.) at 700 RPM for 10 minutes; (3) adding 776.2 g of AEI/CHA SAPO intergrowth over flocculated molecular sieve having a debris factor of 0.23 (LOI: 48.98%) and mixing using Yamato mixer at 700 RPM for 10 minutes, then milling using a Silverson L4RT-A high-shear mixer (Silverson Machines Inc., East Longmeadow, Mass.) at 6000 RPM for 3 minutes; (4) adding 404.2 g of Hydrite UF kaolin clay from Imerys, Rosswell, Ga. (LOI: 15.13%) while mixing using Yamato mixer at 700 RPM. This led to a very growth over flocculated molecular sieve having a debris factor of 0.23 (LOI: 40.62%) and mixing using Yamato mixer at 700 RPM for 5 minutes, then milling using a Silverson L4RT-A high-shear mixer (Silverson Machines Inc., East Longmeadow, Mass.) at 6000 RPM for 3 minutes; (4) adding 427.4 g of Hydrite UF kaolin clay from Imerys, Rosswell, Ga. (LOI: 15.13%) while mixing using Yamato mixer at 700 RPM. This led to a slurry, having 46.5% solids content, 45% sieve, 13.5% alumina binder, and 39% clay and 2.5% $P_2O_5$ derived from $H_3PO_3$. This slurry was milled using a Silverson L4RT-A in-line mixer at 7500 RPM for 75 minutes operated in a circulation mode. The viscosity of the slurry was measured at 10 RPM using a Brookfield Viscometer, Model DV-II+PRO, spindle number 6. Properties of the slurry are given in Table 2. The slurry was spray dried using a Yamato DL-41 spray dryer (Yamato Scientific America, Orangeburg, N.Y.). An amount of 500-750 g of the slurry was spray dried. The spray dryer operated in a down spray mode using an atomization nozzle of 1 mm. The spray drying conditions were: feed rate: 40 g/min; inlet temperature: 350° C.; atomization pressure: 1 bar; carrier gas (nitrogen) flow at 60% of full setting. Spray dried products were collected in a cyclone. They were calcined in a muffle furnace at 650° C. in air for 2 hours. The resulting catalyst had an ARI of 0.29%/hr.

TABLE 2

Properties of Slurries Prepared Using a High-Shear Mixer and Spray Dried Products of Examples 4 & 5

| | Other Slurry Properties | | | | | | | Spray Dried Product | | |
|---|---|---|---|---|---|---|---|---|---|---|
| Ex. | Solids Content wt % | Sieve wt % | ACH-Al$_2$O$_3$ | Clay % | P$_2$O$_5$ % | pH of Slurry | Viscosity (cPs) @ 10 RPM | ARI (wt %/hr) | ABD (g/cc) | MSA (m$^2$/g) |
| 4 | 44 | 45 | 13.5 | 39 | 2.5 | 3.28 | 12,000 | 0.49 | 0.83 | 227.9 |
| 5 | 46.5 | 45 | 13.5 | 39 | 2.5 | 3.34 | 2,500 | 0.29 | 0.87 | N/A |

While the present invention has been described and illustrated by reference to particular embodiments, those of ordinary skill in the art will appreciate that the invention lends itself to variations not necessarily illustrated herein. For example, it is contemplated that a combination of one or more molecular sieves recovered in the presence of one or more flocculants and one or more phosphorous compounds can be used. For this reason, then, reference should be made solely to the appended claims for purposes of determining the true scope of the present invention.

We claim:

1. A process for producing one or more olefin(s), the process comprising the steps of:
   (a) introducing a feedstock comprising one or more oxygenates to a reactor system in the presence of a molecular sieve catalyst composition prepared by the method comprising the steps of:
      (i) combining:
         (A) an over flocculated molecular sieve;
         (B) a binder; and
         (C) optionally, a matrix material;
      to form a catalyst slurry; and
      (ii) milling the catalyst slurry;
   (b) withdrawing from the reactor system an effluent stream; and
   (c) passing the effluent stream through a recovery system recovering at least the one or more olefin(s).

2. The process of claim 1 wherein the over flocculated molecular sieve is recovered with a first flocculant.

3. The process of claim 2 wherein the first flocculant has an average molecular weight (MW) in the range of about 500 to about 50,000,000.

4. The process of claim 1 wherein the over flocculated molecular sieve is synthesized from a synthesis mixture comprising a silicon source, a phosphorous source and an aluminum source, optionally in the presence of a templating agent.

5. The process of claim 1 wherein the over flocculated molecular sieve is present in an amount of about 5 to 95 wt % based on the total weight of the molecular sieve.

6. The process of claim 1 wherein the molecular sieve catalyst composition is prepared by further combining a phosphorous compound.

7. The process of claim 6 wherein the phosphorous compound comprises an acidic phosphorous compound.

8. The process of claim 6 wherein the phosphorous compound is selected from phosphoric acid, phosphorous acid, polyphosphoric acid, ammonium dihydrogen phosphate, ammonium hydrogen phosphate, pyrophosphoric acid, ortho-phosphoric acid, hypophosphorous acid.

9. The process of claim 6 wherein the phosphorus compound is in the range of from about 0.03 wt % to about 20 wt % P$_2$O$_5$ based on the total weight of the molecular sieve(s) and phosphorous compound comprising the catalyst composition.

10. The process of claim 1 wherein the over flocculated molecular sieve is selected from one or more of the group consisting of: a metalloaluminophosphate, a silicoaluminophosphate, an aluminophosphate, a CHA framework-type molecular sieve, an AEI framework-type molecular sieve and a CHA and AEI intergrowth or mixed framework-type molecular sieve.

11. The process of claim 1 wherein the molecular sieve catalyst composition has an ARI of less than about 1.0 weight %/hour.

12. The process of claim 1 wherein the over flocculated molecular sieve has a debris factor, Φ, greater than about 0.2.

13. The process of claim 1 wherein greater than 1000 kg of one or more olefin(s) is being produced.

14. The process of claim 1 wherein the one or more olefin(s) include ethylene and propylene.

15. The process of claim 1 wherein the molecular sieve catalyst composition is prepared by further combining a non-over flocculated molecular sieve.

16. The process of claim 15 wherein the non-over flocculated molecular sieve is recovered with a second flocculant.

17. The process of claim 16 wherein the second flocculant has an average molecular weight (MW) in the range of about 500 to about 50,000,000.

18. The process of claim 15 wherein the non-over flocculated molecular sieve is present in an amount of about 0 to 95 wt % based on the total weight of the molecular sieve.

19. The process of claim 15 wherein the non-over flocculated molecular sieve is selected from one or more of the group consisting of: a metalloaluminophosphate, a silicoaluminophosphate, an aluminophosphate, a CHA framework-type molecular sieve, an AEI framework-type molecular sieve and a CHA and AEI intergrowth or mixed framework-type molecular sieve.

20. The process of claim 15 wherein the molecular sieve catalyst composition has a weight ratio of the non-over flocculated molecular sieve to the over flocculated molecular sieve of about 1:20 to 20:1.

21. The process of claim 1 further comprising the steps of:
   passing a hydrocarbon feedstock to a syngas production zone to produce a synthesis gas stream; and
   contacting the synthesis gas stream with a catalyst to form the feedstock comprising one or more oxygenates.

22. The process of claim 1 wherein the process further comprises the step of:
   polymerizing the one or more olefin(s) in the presence of a polymerization catalyst into a polyolefin.

23. The process of claim 21 wherein the process further comprises the step of:

polymerizing the one or more olefin(s) in the presence of a polymerization catalyst into a polyolefin.

24. The process of claim 21 wherein the feedstock comprising one or more oxygenates comprises methanol, the one or more olefin(s) include ethylene and propylene, and the over flocculated molecular sieve is a silicoaluminophosphate molecular sieve.

25. The process of claim 21 wherein the molecular sieve catalyst composition is prepared by further combining a non-over flocculated molecular sieve.

26. The process of claim 1 wherein the catalyst slurry has a viscosity less than about 10,000 cPs at 10 RPM.

27. The process of claim 26 wherein the catalyst slurry has a viscosity less than about 7,000 cPs at 10 RPM.

28. The process of claim 1 wherein the catalyst slurry has a solids content greater than about 40%.

29. The process of claim 1 wherein the catalyst slurry further comprises a second flocculated molecular sieve having a slurry viscosity of at least 1,000 cPs less than the over flocculated molecular sieve.

30. The process of claim 29 wherein the second flocculated molecular sieve comprises a non-over flocculated molecular sieve.

* * * * *